United States Patent [19]

Williams

[11] Patent Number: Plant 6,820

[45] Date of Patent: May 30, 1989

[54] ORANGE MARMALADE ROSE PLANT

[75] Inventor: J. Benjamin Williams, Silver Spring, Md.

[73] Assignee: NPI, Salt Lake City, Utah

[21] Appl. No.: 153,702

[22] Filed: Feb. 8, 1988

[51] Int. Cl.[4] ..... A01H 5/00

[52] U.S. Cl. ..... Plt./7

[58] Field of Search ..... Plt./7

*Primary Examiner*—Robert E. Bagwill

[57] ABSTRACT

A new and distinct variety of rose plant of the miniature rose class, which was originated by my crossing Gingersnap as seed parent and Orange Honey as pollen parent; characterized by a vivid orange-gold shingle-like bloom accented by a striking deep yellow center and corresponding deep yellow at the point of attachment. The flowers are produced singly and in miniature grandiflora-type sprays on vigorous, upright plants having very attractive deep green, waxy foliage. Fragrance is slightly fruity.

1 Drawing Sheet

The present invention relates to a new and distinct variety of rose plant of the miniature rose class named "Orange Marmalade," which was originated by my crossing as seed parent as unnamed seedling of "Gingersnap" (U.S. Plant Pat. No. 4,330) and the rose known as "Orange Honey" as pollen parent.

Among the novel characteristics possessed by this new variety which distinguishes it from all other varieties of which I am aware are:

1. Flowers of deep orange gold, possessing an almost fluorescent characteristic, with yellow at base of reverse.
2. The full, round buds are slightly cupped and open to flowers approximately 1¼ to 1½". Flowers open in a shingle-like arrangement of ovoid petals which do not recurl. The flower is a vibrant orange-gold with a large yellow open center when bloom is fully mature.
3. This medium-sized plant produces its flowers singly and in miniature grandiflora-type sprays.
4. The plant is sturdy, vigorous and upright with large, dark green, waxy foliage, growing 12–18" in height.
5. The vibrant orange blooms emit a light fruity fragrance.

Asexual reproduction by budding of the new variety as performed in Silver Spring, Md., and West Grove., Pa., shows that the foregoing and other distinguishing characteristics come true to form and are established and transmitted through succeeding propagation.

The new and improved rose variety which I have developed is a vibrant orange-gold flower, opening in a shingle-like arrangement with a large yellow center. Outer edges of petals turn a burnished red in sunlight. Blooms are borne singly on long, strong cutting canes, and in miniature grandiflora-type sprays. This sturdy plant is vigorous and upright, and enhanced by excellent, large, dark green, waxy foliage. The vibrant orange of the blooms makes the plant ideal for color accents in the garden and in arrangements.

The accompanying drawing shows typical specimens of the vegetative growth and flowers of the new variety in different stages of development and as depicted in color as nearly true as it is reasonably possible to make the same in a color illustration of this character.

The following is a detailed description of my new variety, with color terminology in accordance with the Royal Horticultural Society Colour Chart (RHSCC). The terminology used in color description herein refers to plate numbers in the aforementioned color chart, e.g., "32-A" is plate 32-A of the Royal Horticultural Society Colour Chart.

Parentage: Seedling.

*Seed parent.*—An unnamed seedling of "Gingersnap".

*Pollen parent.*—"Orange Honey".

Class: Miniature.

The following observations are made of specimens grown outdoors at Silver Spring, Md. and West Grove, Pa. during the months of June through September.

FLOWER

Blooming habit: Continuous.

A. Bud:
- (1) *Size.*—Medium.
- (2) *Form.*—Full, round and slightly cupped.
- (3) *Color.*—When sepals first divide: near 34-A. When petals begin to unfurl, blending to 20-B at the point of attachment.
- (4) *Sepals.*—Extends well beyond bud.
- (5) *Peduncle.*—Length 3¼–3½ cm. Aspect—straight. Strength—heavy. Color.—146-A.

B. Bloom:
- (1) *Size.*—1¼ to 1½.
- (2) *Borne.*—Individually and in miniature grandiflora-type sprays.
- (3) *Form.*—Opening flat, with petals arranged in a shingle-like effect.
- (4) *Petalage.*—16–18.
- (5) *Color.*—During first two days. Center of Flower — near 20-B. Outer petals near 32-C. Base of petals: near 20-B. Reverse of petals — near 32-B blending to 20-B.
- (6) *Color change.*—General tonality from a distance is a vibrant orange gold accented by a bright yellow center. Color is well maintained.

C. Petals:
- (1) *Texture.*—Thick.
- (2) *Appearance.*—Satiny.
- (3) *Form.*—Ovoid with a moderate tip.
- (4) *Arrangement.*—Regularly arranged shingle-like overlay.
- (5) *Petaloids in center.*—Few.

(6) *Persistence.*—Drops off cleanly.
(7) *Fragrance.*—Light fruity fragrance.
(8) *Lasting quality.*—6–10 days on plant, 3–5 days as cut flower.

REPRODUCTIVE ORGANS

A. Stamens, anthers: Irregularly arranged around styles.
(1) *Color.*—Yellow-orange, near to 21-B.
B. Pollen: Color is a golden yellow, near to 10-A.
C. Styles: Thin, medium length.
D. Stigmas:
*Color.*—Orange-red — 14-C.
E. Hips: Green and globular, ripening to bright orange.

PLANT

A. Form: Upright.
B. Growth: Very vigorous.
*Height attained.*—12–18 in.
C. Foliage: Compound of 5 to 7 leaflets.
(1) *Size.*—Large.
(2) *Quantity.*—Abundant.
(3) *Color.*—New foliage: upper side — 131-A, under side — 138-B. Old foliage: upper side — 131-B, under side — 138-C.
(4) *Shape.*—Oval, pointed.
(5) *Texture.*—Upper side — glossy, smooth. Under side — rough and dull.
(6) *Edge.*—Serrated.
(7) *Serration.*—6 per cm.

(8) *Leaf stem.*—Color — 137-C; under side — 137-D.
(9) *Stipules.*—Medium and bearded.
D. Wood:
(1) *New wood.*—Color — 137-B. Bark — smooth.
(2) *Old wood.*—Color — 137-C. Bark — smooth.
E. Thorns:
(1) *Thorns.*—Quantity: on main stalks from base — ordinary; on laterals from stalk — very few. Form: flat base, pointed slightly downward. Length: long. Color when young — 165-A. Position: irregular.
(2) Prickles.—Quantity: On main stalks — few; on laterals — none.
F. Plant's disease resistance:
(1) *Mildew.*—Outstanding.
(2) *Blackspot.*—Outstanding.
(3) *Rust.*—None observed.
G. Winter hardiness: Completely winter hardy.

I claim:

1. A new and distinct variety of rose plant of the miniature rose class, substantially as shown and described, characterized particularly as to novelty by its vibrant orange-gold petals arranged in a shingle-like arrangement, blending to a large deep yellow center, with a corresponding deep yellow at the point of attachment; its large, waxy, dark-green foliage; its habit of blooming singly on long, strong cutting canes and in miniature grandiflora-type sprays; its light fruity fragrance; its vigorous habit of growth and hardiness; and good holding quality.

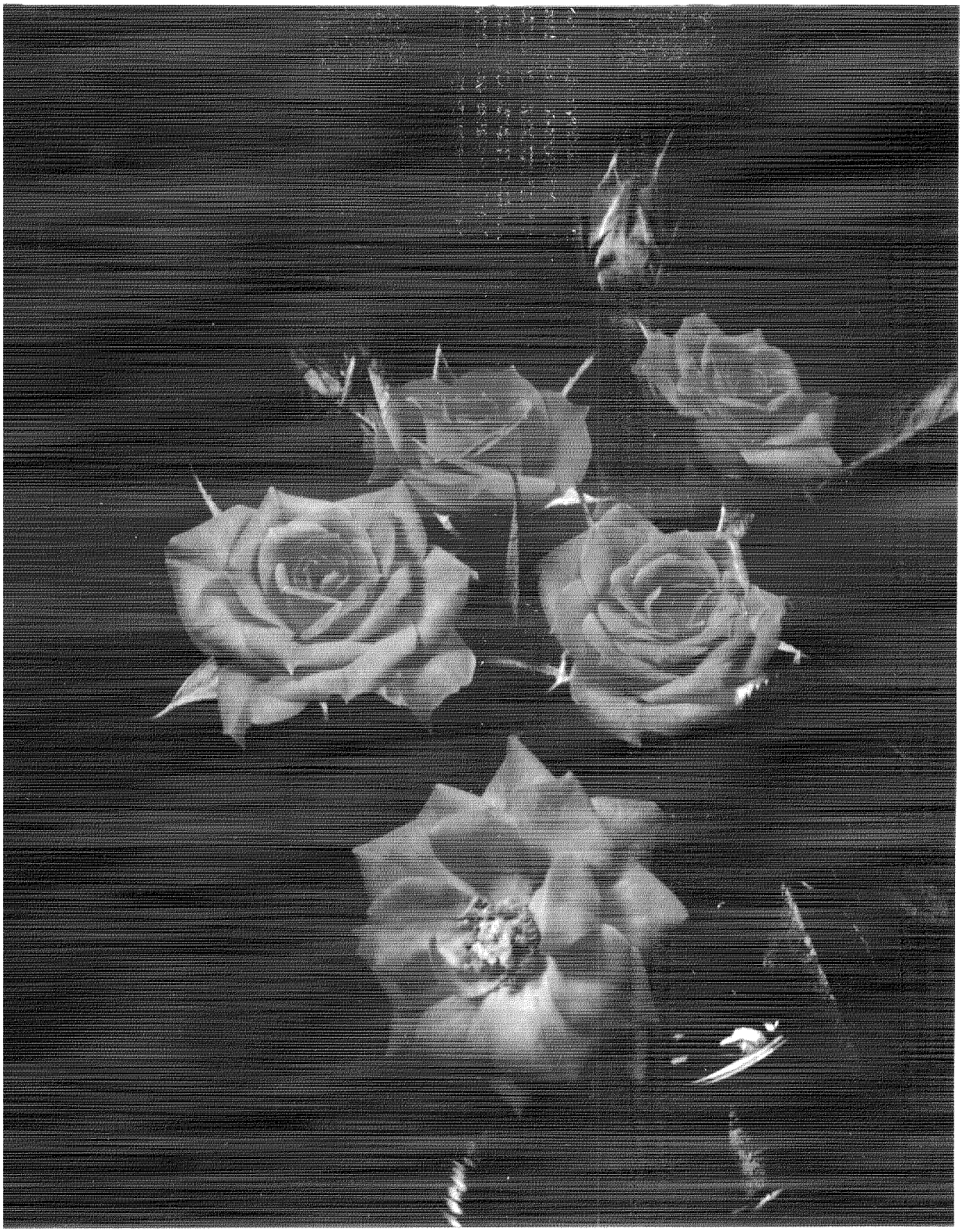

* * * * *